United States Patent [19]

Bengtsson et al.

[11] Patent Number: 5,693,630
[45] Date of Patent: Dec. 2, 1997

[54] PHENYLETHYL AND PHENYLPROPYLAMINES

[75] Inventors: Stefan Bengtsson; Sven Hellberg, both of Södertälje; Nina Mohell, Spånga; Lian Zhang, Södertälje; Gerd Hallnemo, Södertälje; David Jackson, Södertälje; Bengt Ulff, Södertälje, all of Sweden

[73] Assignee: Astra Aktiebolag, Sodertalje, Sweden

[21] Appl. No.: 325,279

[22] PCT Filed: Sep. 16, 1994

[86] PCT No.: PCT/SE94/00860

§ 371 Date: Oct. 26, 1994

§ 102(e) Date: Oct. 26, 1994

[87] PCT Pub. No.: WO95/09835

PCT Pub. Date: Apr. 13, 1995

[30] Foreign Application Priority Data

Oct. 7, 1993 [SE] Sweden ................. 9303274

[51] Int. Cl.$^6$ .............. C07C 232/62; C07C 237/14; C07C 237/16; C07C 237/04

[52] U.S. Cl. .............. 514/183; 514/210; 514/212; 514/327; 514/328; 514/330; 514/409; 514/423; 514/424; 514/425; 514/613; 514/617; 514/623; 514/624; 540/450; 540/451; 540/526; 540/531; 540/607; 546/216; 546/219; 546/226; 548/408; 548/540; 548/546; 548/550; 548/953; 564/123; 564/181; 564/185; 564/188; 564/190

[58] Field of Search .............. 564/123, 185, 564/188, 190, 181; 540/451, 526, 531; 546/216, 219; 548/546, 550, 408; 514/183, 212, 327, 328, 424, 425, 613, 623, 624, 409, 617

[56] References Cited

U.S. PATENT DOCUMENTS

| | | | |
|---|---|---|---|
| 3,712,924 | 1/1973 | Kruger et al. | 564/157 |
| 3,948,898 | 4/1976 | Kutter et al. | 544/363 |
| 4,021,558 | 5/1977 | Kutter et al. | 514/309 |
| 4,490,369 | 12/1984 | Reiffen et al. | 514/213 |
| 4,855,302 | 8/1989 | Gasc et al. | 514/278 |

FOREIGN PATENT DOCUMENTS

| | | |
|---|---|---|
| 0065229 | 6/1982 | European Pat. Off. |
| 7644M | 2/1970 | France. |
| 2396742 | 7/1978 | France. |
| 2345423 | 3/1975 | Germany. |

OTHER PUBLICATIONS

Redeuilh et al., Chemical Abstracts, vol. 83, abstract 97690, 1975.

Hocquaux et al., Chemical Abstracts, vol. 100, abstract 103716, 1983.

(List continued on next page.)

*Primary Examiner*—Richard L. Raymond
*Attorney, Agent, or Firm*—White & Case

[57] ABSTRACT

Compounds of the general formula

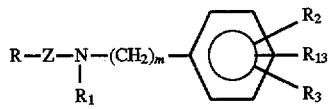

or pharmaceutically acceptable salts thereof, wherein Z is a saturated or unsaturated 3 to 6 carbon chain, m is 2 or 3, $R_1$ is a hydrogen atom, or a straight or branched $C_{1-4}$ alkyl group, $R_2$, $R_3$ and $R_{13}$ are situated in the ortho, meta, or para position of the phenyl ring and are the same or different and selected from the following groups: H, OH, $OR_{14}$, halogen, $CO_2R_9$, CN, $CF_3$, $NO_2$, $NH_2$, $COCH_3$, $OSO_2CF_3$, $OSO_2CH_3$, $CONR_{10}R_{11}$, $OCOR_{12}$, wherein $R_9$, $R_{12}$ and $R_{14}$ is a straight or branched $C_{1-4}$ alkyl group, $R_{10}$ and $R_{11}$ are the same or different and represents hydrogen or a straight or branched $C_{1-6}$ alkyl group, R is 1)

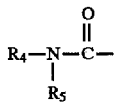

or

2)

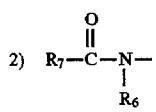

or

3)

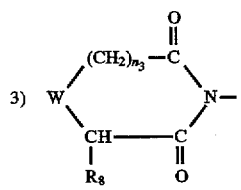

or

4)

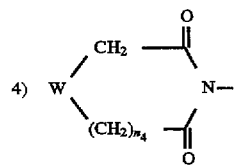

wherein the variables are defined in the specification, processes for their preparation, pharmaceutical preparations containing them and the use of the compounds in the treatment psychiatric disorders.

10 Claims, No Drawings

OTHER PUBLICATIONS

Podona et al., "Synthese de N–(2–Hydroxyethyl)iminoglutarimides à partir de N–(2–Bromoèthyl)glutarimides," Tetrahedron, vol. 49, No. 21, pp. 4619–4626 (1993).

Chemical Abstracts, vol. 55, "17634g hydroxyanthranilic Acid: A Potent Inhibitor of 3–Hydroxyanthranilic Acid Oxidase," Archives of Biochemistry and Biophysics, vol. 203, No. 1, pp. 161–166 (1980).

PHENYLETHYL AND PHENYLPROPYLAMINES

This application is a 371 of PCT/SE94/00860, filed Sep. 16, 1994.

FIELD OF THE INVENTION

The present invention relates to novel, phenylethylamines and phenylpropylamines, and processes for their preparation, pharmaceutical compositions containing the phenylethylamines and phenylpropylamines and the use of said compounds in therapy.

The object of the present invention is to provide novel compounds that will be useful in the treatment of psychiatric disorders such as schizophrenia and other psychoses, anxiety, depression and manic-depressive psychosis.

PRIOR ART

The French patent application M 7.430 describes compounds of the formula

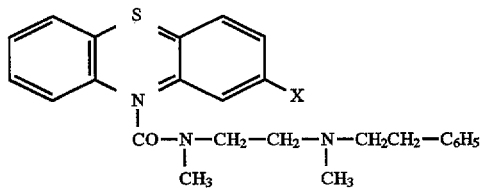

wherein X is a hydrogen or chlorine atom. The compounds have neurosedative and spasmolytic effects.

From the U.S. Pat. No. 4,833,138 compounds of the formula

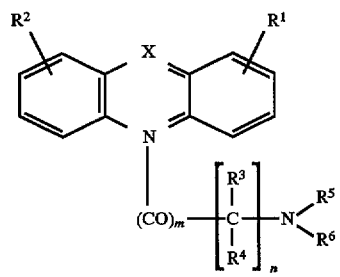

are known.

According to the patent each of $R^1$ and $R^2$ is one or more groups independently selected from hydrido, hydroxyalkyl, haloalkyl acyl, cykloalkyl, cycloalkylalkyl, haloalkylsulfonyl, alkylcarbonyl, halo, alkylthio, phenylalkyl, phenylalkylthio, cyano, nitro, amino, alkylamino, sulfono, alkylaminosulfonyl, amido, alkylamido, hydroxyimino, hydroxyiminoalkyl, carboxyl, carboxylalkyl, carboxylalkenyl, thiazolyl, methylthiazolyl, alkoxycarbonylamino, alkylaminosulfonylamino, aminocarbonyliminoalkyl, haloalkylcarbonyl, morpholinoalkylcarbonyl, aminothiazolyl, morpholinothiocarbonylalkyl, dioxycycloalkylalkyl, cyclopropylcarbonyl, tetrazolylalkyl, iminoalkyl and hydroxyiminoalkyl; wherein each of $R^3$ through $R^6$ is independently selected from hydrido, alkyl, alkoxy, alkenyl, hydroxyalkyl, alkylaminoalkylcarbonyl, alkoxyalkyl, glycyl, aminoalkyl, alkylaminothioalkyl, aminoalkylcarbonyloxy, cyano, phenylalkyl, phenylalkyloxyalkyl, cycloalkyl, haloalkyl, morpholinoalkylalkyl, piperazinylalkyl, azepinylalkyl, phenylalkylaminoalkylamido, alkylaminocarbonyloxyalkyl, piperidinylalkyl and piperidinylalkylaminoalkylcarbonyl; wherein X is selected from sulfur, sulfinyl and sulfonyl; wherein m is zero or one; and wherein n is an integer from one through five.

The compounds have effect on the prevention of neurodegenerative consequences associated with conditions of hypoxia or ischemia.

Furthermore it is known from the French patent M 7.644 that the compounds of the formula

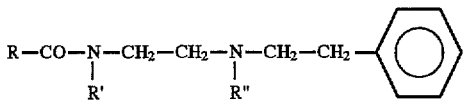

wherein R represents a group

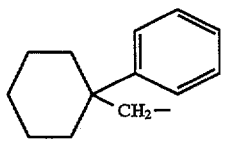

a)

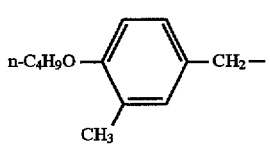

b)

or

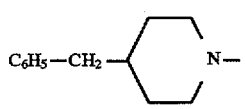

c)

and R' and R" represent a smaller alkyl preferably methyl, or together form a second bond —$CH_2$—$CH_2$— between the two nitrogen atoms. The compounds have spasmolytic effect.

In the Journal of Medicinal Chemistry, 1989, 32, 1921–1926, Glennon and coworkers describe some compounds of the formula

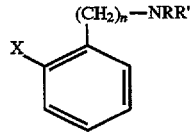

wherein X is hydrogen or methoxy, n is 2 or 3, R' is methyl or hydrogen and R is methyl or N-[4-(2-phtalimido)butyl]. The compounds have some affinity for the 5-$HT_{1A}$ receptor.

In Bull. Chim. Soc. Fr. 1975, (3-4, Pt.2), 846–9 some compounds of the formula

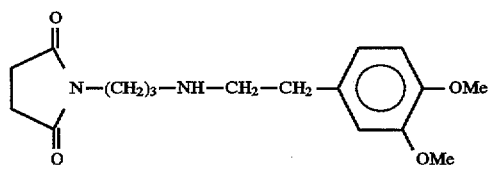

are described. These compounds are used as intermediates in the preparation of 8,13-diazasteroids.

In Khim. Geterotsikl. Soedin. 1986, (4), 514–17 (CA 106 (15): 119843z) some compounds of the formula

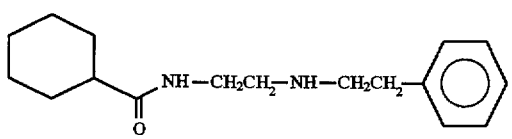

are described, These compounds are used as starting material in the synthesis of 1-aralkyl-4-acyl-2-piperazinones.

DISCLOSURE OF THE INVENTION

According to the present invention it has been found that new compounds of the general formula I

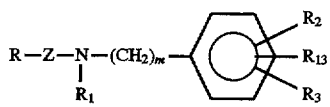

or pharmaceutically acceptable salts thereof, wherein

Z is a saturated or unsaturated 3 to 6 carbon chain, m is 2 or 3, $R_1$ is a hydrogen atom, or a straight or branched $C_{1-4}$ alkyl group, $R_2$, $R_3$ and $R_{13}$ are situated in the ortho, meta, or para position of the phenyl ring and are the same or different and selected from the following groups: H, OH, $OR_{14}$, halogen, $CO_2R_9$, CN, $CF_3$, $NO_2$, $NH_2$, $COCH_3$, $OSO_2CF_3$, $OSO_2CH_3$, $CONR_{10}R_{11}$, $OCOR_{12}$, wherein $R_9$, $R_{12}$ and $R_{14}$ is a straight or branched $C_{1-4}$ alkyl group, $R_{10}$ and $R_{11}$ are the same or different and represents hydrogen or a straight or branched $C_{1-6}$ alkyl group, R is 1)

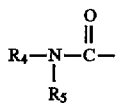

wherein $R_4$ and $R_5$ are the same or different, and, when different represent a hydrogen atom, a straight or branched $C_{1-5}$ alkyl group, or a substituted or unsubstituted cycloalkyl group, and, when the same, represent a straight or branched $C_{1-5}$ alkyl group, or $R_4$ and $R_5$ are together —$(CH_2)n_1$—, where $n_1$ is 3–7, or

2)

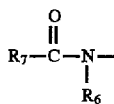

wherein $R_6$ is a hydrogen atom, a straight or branched $C_{1-6}$ alkyl group, and $R_7$ is a substituted or unsubstituted cycloalkyl group or $R_6$ and $R_7$ are together —$(CH_2)n_2$—, where $n_2$ is 3–6, or

3)

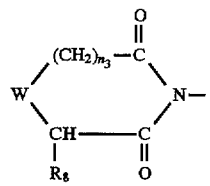

wherein W is an optionally substituted carbocyclic ring(s) or an optionally substituted methylene group, and $R_8$ is a straight or branched $C_{1-5}$ alkyl group or a phenyl group, $n_3$ is 0–2 or

4)

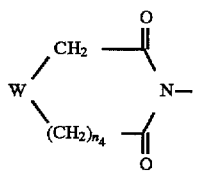

wherein W is an optionally substituted carbocyclic ring(s), or an optionally substituted methylene group and $n_4$ is 1 or 2, in racemic or optically active form, exhibit an affinity for $D_3$ receptors. Some of the compounds also exhibit affinity for 5-$HT_{1A}$ and $D_2$ receptors. These effects makes it possible to use the compounds defined above in the treatment of mental disturbances e.g. psychosis, schizophrenia and depression.

$R_2$, $R_3$ and $R_{13}$ in the definition above are preferably hydrogen, methoxy, ethoxy, halogen, CN, $CONR_{10}R_{11}$, $CF_3$, nitro, or amino; $R_{10}$ and $R_{11}$ are preferably hydrogen, methyl or ethyl.

Halogen in the definition above is preferably fluorine, chlorine or bromine.

Z in the definition above is when saturated preferably a 3 to 6 carbon chain and when unsaturated a 4 to 6 carbon chain.

$R_4$ and $R_5$ in the definition above are preferably the same and a straight or branched $C_{1-4}$ alkyl group, or $R_4$ and $R_5$ are together —$(CH_2)n_1$, $n_1$ is preferably 4 to 6.

$R_6$ in the definition above is preferably a hydrogen atom or a $C_{1-3}$ alkyl group.

A carbocyclic ring(s) in the definition above is preferably a mono, bi or polycyclic ring(s) having 5–10 carbon atoms, such as cyclopentyl, cyclohexyl, or cycloheptyl.

The substituents on the carbocyclic ring(s) in the definition above are preferably a hydrogen atom or a straight or branched $C_{1-4}$ alkyl group(s).

A cycloalkyl group in the definition above is preferably a $C_3$–$C_{12}$ mono, bi or polycylic ring(s) such as adamantyl, cycloheptyl, cyclohexyl, cyclopentyl, bicyclooctyl, bicycloheptyl, bicyclononyl, bicycloheptenyl, bicyclooctenyl, bicyclononenyl.

The substituents on the methylene group in the definition above are preferably a hydrogen atom or a $C_{1-4}$ alkyl group(s).

Most preferred are the following compounds:

8-(4-{[2-(4-Amino-3-trifluoromethylphenyl)ethyl] methylamino}butyl)-8-aza-spiro[4.5]decane-7,9-dione oxalate Cyclohexanecarboxylic acid (4-{[2-(3,4-dimethoxyphenyl)ethyl]propylamino}butyl)amide Cyclohexanecarboxylic acid (4-{[2-(5-bromo-2-methoxyphenyl)ethyl]propylamino}butyl)amide oxalate Bicyclo[2.2.2]octane-1-carboxylic acid (6-{[2-(4-amino-3-trifluoromethylphenyl)ethyl]methylamino}hexyl)amide hydrochloride Bicyclo[2.2.2]octane-1-carboxylic acid (4-{isopropyl-[2-(2-methoxyphenyl)ethyl]amino}butyl)amide Adamantane-1-carboxylic acid (4-{[2-(2-methoxyphenyl)ethyl]propylamino}butyl)amide oxalate Cyclohexanecarboxylic acid (4-{[2-(2-chloro-4-methoxyphenyl)ethyl]propylamino}butyl)amide oxalate Adamantane-1-carboxylic acid (4-{[2-(2,4-dimethoxyphenyl)ethyl]propylamino}butyl)amide oxalate

PREPARATION

Compounds of the general formula I

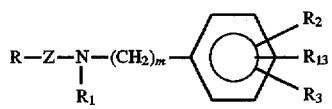

wherein R, $R_1$, $R_2$, $R_3$, $R_{13}$, Z and m are as defined above are prepared by any of the following alternative methods:

A. Reaction of a compound of the general formula II

wherein R and Z are as defined above and X is a suitable leaving group such as halogen, arylsulfonate or alkylsulfonate or X is a group

wherein Y is hydrogen, hydroxy, halogen or alkoxy with a compound of the general formula III

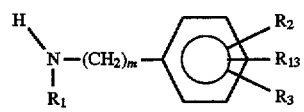

wherein $R_1$, $R_2$, $R_3$, $R_{13}$ and m are as defined above in a suitable solvent, such as an alcohol, DMF, acetonitrile or DMSO in the presence of a base such as triethylamine, sodium hydroxide, or potassium carbonate and a catalytic amount of a sodium or potassium halide, such as KI at ambient or higher temperature for a prolonged time or in the presence of a suitable reducing agent such as sodium cyanoborohydride or lithium aluminium hydride in a direct or stepwise manner.

B. Reaction of a compound of the general formula IV

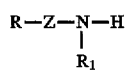

wherein R, Z and $R_1$ are as defined above with a compound of the general formula V

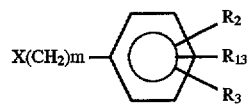

wherein X, m, $R_2$, $R_3$ and $R_{13}$ are as defined above in a suitable solvent, such as an alcohol, DMF, acetonitrile or DMSO in the presence of a base such as triethylamine, sodium hydroxide, or potassium carbonate and a catalytic amount of a sodium or potassium halide, such as KI at ambient or higher temperature for a prolonged time or in the presence of a suitable reducing agent such as sodium cyanoborohydride or lithium aluminium hydride in a direct or stepwise manner.

C. Reaction of a compound of the general formula VI

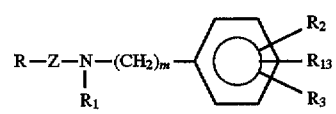

wherein R, Z, m, $R_2$, $R_3$ and $R_{13}$ are as defined above with a compound of the general formula VII $$R_1 X \qquad \text{VII}$$

wherein $R_1$ and X are as defined above in a suitable solvent, such as an alcohol, DMF, acetonitrile or DMSO in the presence of a base such as triethylamine, sodium hydroxide, or potassium carbonate and a catalytic amount of a sodium or potassium halide, such as KI at ambient or higher temperature for a prolonged time or in the presence of a suitable reducing agent such as sodium cyanoborohydride or lithium aluminium hydride in a direct or stepwise manner.

D. Reaction of a compound of the general formula VIII

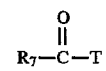

wherein $R_7$ is as defined above and T represents a suitable acid derivative, such as halide, ester or other acid activating group, or of a compound of the general formula IX

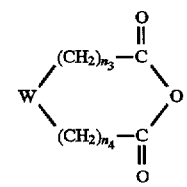

wherein W, $n_3$ and $n_4$ are as defined above, with a compound of the general formula X

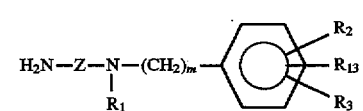

wherein Z, $R_1$, $R_2$, $R_3$, $R_{13}$ and m are as defined above in a suitable solvent such as dichloromethane, chloroform, toluene, acetic acid, or tetrahydrofuran or neat at ambient or elevated temperature for a prolonged time.

E. Conversion of a compound of the general formula XI

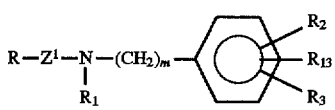

wherein R, $R_1$, $R_2$, $R_3$, $R_{13}$ and m are as defined above and $Z^1$ represents an unsaturated 3–6 carbon chain to a compound of the general formula I

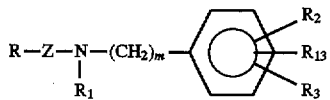

wherein R, $R_1$, $R_2$, $R_3$, $R_{13}$, Z and m are as defined above with a suitable reducing agent such as hydrogen, hydrides, boranes, sodium in $NH_3$ or zinc in the presence of suitable catalytic reagent such as palladium, platinum, nickel salts, lead salts, cuprous salts in a suitable solvent such as ethanol, THF, toluene, HMPT at an ambient or elevated temperature for a prolonged time.

F. Conversion of a compound of the general formula XII

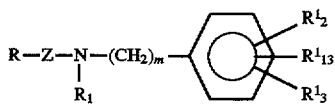

wherein R, $R_1$, Z and m are as defined above and $R^1_2$, $R^1_3$ and $R^1_{13}$ represent substituents that can be modified by suitable reactions such as reduction, hydrogenation, hydrolysis, demethylation, nitration, esterification, halogenation, acetylation, carbonylation (C=O) or dehydration or other suitable reaction to a compound of the general formula I

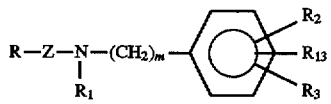

wherein R, $R_1$, $R_2$, $R_3$, $R_{13}$, Z and m are as defined above.

G. Reaction of a compound of the general formula XIII

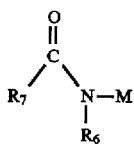

wherein $R_6$ and $R_7$ are as defined above and M represents a suitable alkali metal such as sodium or potassium or of a compound of the general formula XIV

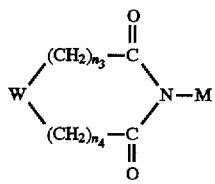

wherein W, $n_3$, $n_4$ and M are as defined above with a compound of the general formula XV

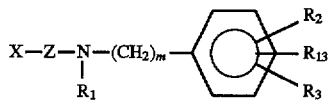

wherein X, Z, $R_1$, $R_2$, $R_3$, $R_{13}$ and m are as defined above in a suitable solvent such as DMF, acetonitrile or DMSO in the presence of a base such as triethylamine, sodium hydroxide or potassium carbonate at ambient or higher temperature for a prolonged time.

H. Reaction of a compound of the general formula XVI

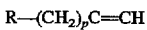

R—$(CH_2)_p$C≡CH wherein R is as defined above and p is 1–3 with paraformaldehyde and a compound of the general formula XVII

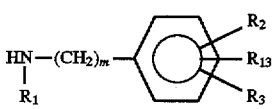

wherein $R_1$, $R_2$, $R_3$, $R_{13}$ and m are as defined above in a suitable solvent such as dioxan, aceton or ethanol in the presence of a suitable catalyst such as copper acetate at ambient or elevated temperature for prolonged time.

PHARMACEUTICAL FORMULATIONS

According to the present invention the compounds of the formula I will normally be administered orally, rectally or by injection, in the form of pharmaceutical preparations comprising the active ingredient either as a free base or a pharmaceutically acceptable non-toxic, acid addition salt, e.g. the hydrochloride, hydrobromide, lactate, acetate, phosphate, sulfate, sulfamate, citrate, tartrate, oxalate and the like in association with a pharmaceutically acceptable dosage form. The dosage form may be a solid, semisolid or liquid preparation. Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical formulations containing a compound of the formula I in the form of dosage units for oral application the selected compound may be mixed with a solid excipient, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin and the like, and then compressed into tablets. If coated tablets are required, the cores, prepared as described above, may be coated with a concentrated sugar solution which may contain, e.g. gum arabic, gelatine, talcum, titanium dioxide, and the like. Alternatively, the tablet can be coated with a polymer well known in the art, dissolved in a readily volatile organic solvent or mixture of organic solvents or in water. Dyestuffs may be added to these coatings in order to readily distinguish between tablets containing different active substances or different amounts of the active compounds.

For the preparation of soft gelatine capsules, the active substance may be admixed with e.g. a vegetable oil or polyethylene glycol. Hard gelatine capsules may contain granules of the active substance using either the above mentioned excipients for tablets e.g. saccharose, sorbitol, mannitol, starches (e.g. potato starch, corn starch or amuylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example, solutions containing from about 0.2% to about 20% by weight of the active substance herein described, the balance being sugar and mixture of ethanol, water, glycerol, and propylene glycol. Optionally such liquid preparations may contain colouring agents, flavouring agents, saccharin and carboxymethylcellulose as a thickening agent or other excipients well known in the art.

Solutions for parenteral applications can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

Suitable daily doses of the compounds of the invention in the therapeutic treatment of humans are 50–500 mg by oral administration and up to 100 mg via parenteral administration.

EXAMPLES

Example 1 (Method A)

8-(4-{[2-(4-Amino-3-trifluoromethylphenyl)ethyl]methylamino}butyl)-8-azaspiro[4.5]decane-7,9-dione oxalate A mixture of N-methyl-4-amino-3-trifluoromethylphenethylamine (520 mg, 2.38 mmol), N-(4-bromobutyl)-8-azaspiro[4,5]decane-7,9 dione (792 mg, 2.6 mmol), potassium carbonate (359 mg, 2.6 mmol), and potassium iodide (catalytic amount) was heated in DMF (25 ml) at 90° C. for 3 h. The solvent was removed in vacuum and the residue taken up in ether and water. The organic phase was separated, dried and the solvent removed to yield 1.11 g of an oil which was purified by chromatography in methanol to yield 460 mg (1.1 mmol) of the pure base. This was dissolved in diisopropyl ether and treated with 130 mg oxalic acid dihydrate and the precipitate recrystallized from diisopropyl ether/ethanol to yield 362 mg (0.7 mmol) of the title compound. M.p. 83°–86° C.

In an analogous way the following compounds (examples 2–34) were prepared:

Example 2

1-(3-{[2-(4-Amino-3-trifluoromethylphenyl)ethyl]propylamino}propyl)-3-phenylpyrrolidine-2,5-dione $^1$H NMR (CDCL$_3$) δ 7.36–7.10 (m, 7 H), 6.66 (d, 1 H), 4.00 (m, 1 H), 3.60 (t, 2 H), 3.13 (dd, 1 H), 2.80 (dd, 1 H), 2.60 (s, 4 H), 2.50 (t, 2 H), 2.43 (t, 2 H), 1.75 (q, 2 H), 1.59 (q, 2 H), 0.87 (t, 3 H).

Example 3

8-(6-{Isopropyl-[2-(2-methoxyphenyl)ethyl]amino}-hexyl-8-aza-spiro[4.5]decane-7,9-dione oxalate M.p. 117°–119° C.

Example 4

8-(4-{Propyl-[3-(2-methoxyphenyl)propyl]amino}butyl)-8-aza-spiro[4.5]decane-7,9-dione $^1$H NMR (CDCl$_3$) δ 7.14 (m, 2 H), 6.84 (m, 2 H), 3.82 (s, 3 H), 3.75 (t, 2 H), 2.58 (s,4 H), 2.40 (m, 12 H), 1.70 (m, 4 H), 1.45 (m, 8 H), 0.82 (t, 3 H).

Example 5

Cyclohexanecarboxylic acid (4-{[2-(3,4-dimethoxyphenyl)ethyl]propylamino}butyl)amide $^1$H NMR (CDCl$_3$) δ 6.79 (d, 1 H), 6.72 (m, 2 H), 6.15 (bs 1 H), 3.86 (s+s, 3+3 H), 3.22 (q, 2 H), 2.67 (bs, 4 H), 2.46 (m, 4 H), 2.03 (m, 1 H), 1.75 (m, 5 H), 1.43 (m, 8 H), 1.23 (m, 3 H), 0.89 (t, 3 H).

Example 6

Cyclohexanecarboxylic acid (4-{[2-(5-bromo-2-methoxyphenyl)ethyl]propylamino}butyl)amide oxalate M.p. 104°–106° C.

Example 7

Adamantane-1-carboxylic acid (4-{[2-(5-methoxy-2-nitrophenyl)ethyl]propylamino}butyl)amide oxalate (NCA 319)

M.p. 144°–148° C.

Example 8

2,2,3,3-Tetramethyl-cyclopropanecarboxylic acid (4-{[2-(3-chloro-2-methoxyphenyl)ethyl]propylamino}butyl)-amide oxalate M.p. 107°–113° C.

Example 9

Adamantane-1-carboxylic acid (4-{[2-(4-chloro-3-methoxyphenyl)ethyl]propylamino}butyl)amide oxalate M.p. 163°–165° C.

Example 10

1-Phenyl-cyclopropanecarboxylic acid (6-{[2-(2-methoxyphenyl)ethyl]methylamino}hexyl)amide oxalate M.p. 60°–64° C.

Example 11

1-Phenyl-cyclopropanecarboxylic acid (4-{[2-(4-amino-3-trifluoromethylphenyl)ethyl]isopropylamino}butyl)-amide dihydrochloride M.p. 180°–181° C.

Example 12

Bicyclo[2.2.2]octane-1-carboxylic acid (6-{[2-(4-amino-3-trifluoromethylphenyl)ethyl]methylamino}hexyl)amide hydrochloride M.p. 54°–58° C.

Example 13

Adamantane-1-carboxylic acid (4-{[2-(2-methoxyphenyl)ethyl]methylamino}butyl)amide oxalate M.p. 78°–82° C.

Example 14

Cyclohexanecarboxylic acid (4-{[2-(2,3-dimethoxyphenyl)ethyl]propylamino}butyl)amide oxalate M.p. 99°–101° C.

Example 15

2,2,3,3-tetramethyl-cyclopropanecarboxylic acid (4-{[2(3-bromo-4-methoxyphenyl)ethyl] propylamino}butyl)amide oxalate M.p. 69°–73° C.

Example 16

Cyclohexanecarboxylic acid (4-{[2-(2-chloro-4-methoxyphenyl)ethyl]propylamino}butyl)amide oxalate (NCA 541)

M.p. 90°–93° C.

Example 17

2,2,3,3-Tetramethyl-cyclopropanecarboxylic acid (4-{[2-(2,5-dimethoxyphenyl)ethyl]propylamino}butyl) amide oxalate M.p. 138°–141° C.

Example 18

Adamantane-1-carboxylic acid (4-{[2-(2,4-dimethoxyphenyl)-ethyl]-propyl-amino}-butyl)-amide oxalate M.p. 132°–134° C.

Example 19

8-(4-{Isopropyl-[2-(2-methoxy-phenyl)-ethyl]-amino}-butyl-8-aza-spiro[4.5]decane-7,9-dione $^1$H NMR (CDCl$_3$) δ 7.14 (m, 2 H), 6.85 (m, 2 H), 3.83 (s, 3 H), 3.77 (m, 2 H), 2.97 (m, 1 H), 2.70 (m, 2 H), 2.58 (m, 6H), 2.46 (m, 2 H), 1.70 (m, 4 H), 1.49 (m, 8 H), 0.99 (d, 6 H).

Example 20

8-(6-{[2-(3-Amino-4-chloro-phenyl)-ethyl]-propyl-amino}-hexyl)-8-aza-spiro[4.5]decane-7,9-dione $^1$H NMR (CDCl$_3$) δ, 7.11 (d, 1 H), 6.60 (d, 1 H), 6.50 (dd, 1 H), 4.02 (bs, 2 H), 3.75 (t, 2 H), 2.58 (s, 6 H), 2.42 (m, 8 H), 1.70 (m, 4 H), 1.58 (m, 8 H), 1.27 (m, 4 H), 0.86 (t, 3 H).

Example 21

Adamantane-1-carboxylic acid (4-{[2-(3-methoxy-phenyl)-ethyl]-propyl-amino}-butyl)-amide oxalate M.p. 131°–135° C.

Example 22

1-(4-{Isopropyl-[2-(2-methoxy-phenyl)-ethyl]-amino}-butyl)-perhydroazepin-2-one $^1$H NMR (CDCl$_3$) δ 7.15 (dd, 2 H), 6.85 (dd, 2 H), 3.82 (s, 3 H), 3.30 (m, 4 H), 2.98 (m, 1 H), 2.70 (m, 4 H), 2.50 (m, 4 H), 1.68 (m, 6 H), 1.46 (m, 4 H), 0.98 (d, 6 H).

Exampel 23 trans-4-Propylcyclohexanecarboxylic acid, 5-{[-2-(4-nitrophenyl)ethyl]-propylamino}pentylamide oxalate M.p. 101°–105° C.

Example 24 trans-4-Propylcyclohexanecarboxylic acid, 5-{[2-(4-amino-3,5-dibromophenyl)ethyl] propylamino}pentylamide oxalate M.p. 131°–135° C.

Example 25 trans-4-Propylcyclohexanecarboxylic acid, 5-{[2-(2-chloro-4-nitrophenyl)-ethyl] propylamino}pentylamide M.p. 84°–86° C.

Example 26

Cyclohexanecarboxylic acid, (4-{[2-(3-cyano-4-nitrophenyl)ethyl]propyl-amino}butyl)amide M.p. 48°–52° C.

Example 27

Cyclohexanecarboxylic acid, N-(4-[2-(4-amino-3-trifluoromethylphenyl)-ethyl]propylaminobutyl) amide $^1$H NMR (CDCl$_3$) 7.24 (d, 1 H), 7.14 (dd, 1 H), 6.69 (d, 1 H), 5.77 (broad, 1 H), 3.26–3.20 (m, 2 H), 2.70 (s, 4 H), 2.58–2.50 (m, 4 H), 2.07–1.99 (m, 1 H), 1.86–1.21 (m, 16 H), 0.90 (t, 3 H).

Example 28

Cyclohexanecarboxylic acid, N-(4-[2-(4-amino-3-trifluoromethylphenyl)ethyl]butylaminobutyl)amide $^1$H NMR (CDCl$_3$) 7.24 (d, 1 H), 7.12 (dd, 1 H), 6.67 (d, 1 H), 5.81 (broad, 1 H), 3.26–3.20 (m, 2 H), 2.61 (s, 4 H), 2.45 (t, 4 H), 2.07–1.99 (m, 1 H), 1.86–1.21 (m, 18 H), 0.91 (t, 3 H).

Example 29

Adamantane-1-carboxylic acid, (4-{N-isopropyl-2-(2-methoxy-5-bromophenyl)ethylamino}butylamide oxalate M.p. 40°–50° C.

Example 30

Adamantane-1-carboxylic acid (4-{N-isopropyl-2-(2-methoxy-5-fluorophenyl)ethylamino}butyl)amide hydrochloride $^1$H NMR (CDCl$_3$), base δ 6.83 (m,2H), 6.75 (dd, 1 H), 5.60 (br s, 1 H), 3.78 (s, 3 H), 3.20 (q, 2H), 2.95 (m, 1 H), 2.65 (m, 2 H), 2.57 (m, 2 H), 2.42 (t, 2 H), 2.04 (br s, 3 H), 1.84 (br s, 6 H), 1.71 (m, 6 H), 1.43 (m, 4 H), 0.97 (d, 6 H).

Example 31

Adamantane-1-carboxylic acid (5-{2-(4-methoxyphenyl)ethyl}amino-pentyl)amide

M.p. 63°–64.5° C.

Example 32

[3-{N-propyl-2-(2-chloro-4-methoxyphenyl)ethylamino}-propyl]-2,3-dihydro-1H-isoindole-1,3-dione hydrochloride M.p. 152°–154.5° C.

Example 33

Adamantane-1-carboxylic acid (3-{N-propyl-2-(2-chloro-4-methoxy-phenyl)ethylamino}propyl)amide $^1$H NMR (CDCl$_3$) 7.10 (d, 1 H), 7.01 (br s, 1 H), 6.89 (d, 1 H), 6.75 (dd, 1 H), 3.76 (s, 3 H), 3.32 (q, 2 H), 2.81 (m, 2 H), 2.68 (m, 2 H), 2.60 (t, 2 H), 2.50 (t, 2 H), 2.01 (br s, 3 H), 1.83 (s, 6 H), 1.69 (br s, 6 H), 1.65 (m, 2 H), 1.53 (m, 2 H), 0.90 (t, 3 H).

Example 34 (Method B)

6-{Isopropyl-[2-(2-methoxyphenyl)ethyl]amino}hexanoic acid diisopropylamide

To a solution of 6-phthalimidohexanoic acid (7.83 g, 30 mmol) in 100 mL toluene and 1 mL DMF was added thionyl chloride (7.2 mL, 160 mmol) and the mixture heated at 100° C. for 1 h. After evaporation the residual acid chloride was dissolved in 25 mL methylene chloride and added to diisopropylamine (7.0 g, 70 mmol) in 100 mL methylene chloride at 0–10 C. The mixture was stirred at rt for 2 H, the solvent removed, the residue taken up in ether and extracted with 2N HCl. The organic solvent was removed and the residue recrystallized from diisopropylether/hexane (3:2). Yield 70% of phthalimidohexanoic acid diisopropylamide. Mp 85°–86° C. This amide (1.03 g, 3 mmol) and hydrazinhydrate (250 mg, 5.3 mmol) were heated in ethanol at 80 C. for 6 h. The mixture was cooled and filtered, the solvent removed and the residue taken up in H$_2$O and ethyl acetate. The organic phase yielded 440 mg (70%) of 6-aminohexanoic acid diisopropylamide. This compound (440 mg, 2.0 mmol) was reacted with aceton (240 mg, 6 mmol) and sodium cyanoborohydride (226 mg, 3 mmol) in methanol (pH adjusted to 5–6 with acetic acid) at rt for 5 h. 2 mL 2M HCl was added, the solvent removed and the residue taken up in ether after alkalisation. Yield 400 mg (78%) of 6-isopropylaminohexanoic acid diisopropylamide. This secondary amide (400 mg, 1.6 mmol), 2-methoxyphenethyl bromide (from 2-methoxyphenethylalcohol and PBr$_3$, 516 mg, 2.4 mmol), and potassium carbonate (330 mg, 2.4 mmol) in 20 mL DMF were heated for 20 h. The solvent was removed and the residue purified by flash chromatography in aceton. Yield 180 mg (30%) of the title compound.

$^1$H NMR (CDCl$_3$) 7.15 (m, 2 H), 6.85 (m, 2 H), 3.97 (m, 1 H), 3.82 (s, 3 H), 3.48 (broad, 1 H), 3.00 (m, 1 H), 2.73 (m, 2 H), 2.60 (m, 2 H), 2.46 (t, 2 H), 2.28 (t, 2 H), 1.64 (m, 2H), 1.50 (m, 2 H), 1.38 (d, 6 H), 1.35 (m, 2 H), 1.20 (d, 6 H), 1.00 (d, 6 H).

Example 35 (Method B)

Cyclohexanecarboxylic acid, 4-{[(2-phenylethyl)propylamino]butyl}amide

A mixture of cyclohexanecarboxylic acid, 4-methanesulfonatobutylamide (1.38 g, 5 mmol), propylamine (3.0 g, 50 mmol), and sodium carbonate (1.0 g, 10 mmol) in acetonitrile (30 mL) was heated for 2 h at 80° C. The solvent was removed and the residue taken up in ether and H$_2$O. The organic phase was extracted with 2M HCl, the aqueous phase made alkaline, and the product taken up in ether to yield 510 mg (2.1 mmol) of cyclohexanecarboxylic acid, 4-propylaminobutylamide. This raw material was heated in DMF with 2-bromoethylbenzene (425 mg, 2.3 mmol) and potassium carbonate (317 mg, 2.3 mmol) for 3 h at 80 C. The solvent was removed, the residue taken up in ether and H$_2$O, the organic phase extracted with 2M HCl, and the acid phase made alkaline and extracted with ether, yielding 454 mg (63%) raw material which was purified by flash chromatography (ethyl acetate/triethylamine 100:4).

$^1$H NMR (CDCl$_3$) 7.30–7.16 (m, 5 H), 5.80 (br s, 1 H), 3.22 (q, 2 H), 2.70 (d, 4 H), 2.47 (m, 4 H), 2.03 (m, 1 H), 1.75 (m, 5 H), 1.42 (m, 8 H), 1.23 (t, 3 H), 0.88 (t, 3 H).

Example 36 (Method C)

Adamantane-1-carboxylic acid (5-{N-propyl-2-(4-methoxyphenyl)-ethylamino}pentyl)amide oxalate Propanal (416 L, 6.0 mmol) and sodium cyanoborohydride (200 mg, 3.0 mmol) were added to a solution of adamantane-1-carboxylic acid (5-[2-(4-methoxyphenyl)ethyl]aminopentyl)amide in methanol (15 mL), and the pH adjusted to 5 with acetic acid. After stirring for 2 h at rt, the methanol was removed, ether added and the organic layer washed with 2M NH$_3$ and dried. Evaporation of the solvent gave 630 mg (95%) oil. Addition of oxalic acid (166 mg, 1.3 mmol) to a solution of 580 mg (1.3 mmol) of the base in acetone (10 mL), followed by addition of isopropylether gave 569 mg (85%) white solid after evaporation of all solvent, followed by washing with hexane.

$^1$H NMR (base, CDCl$_3$) 7.11 (d, 2 H), 6.83 (d, 2 H), 5.63 (br s, 1 H), 3.78 (s, 3 H), 3.21 (q, 2 H), 2.65 (br s, 4 H), 2.45 (q, 4 H), 2.03 (br s, 3 H), 1.84 (br s, 6 H), 1.71 (m, 6 H), 1.46 (m, 6 H), 1.31 (m, 2 H).

Example 37 (Method D)

Bicyclo [2.2.2]octane-1-carboxylic acid (4-{isopropyl-[2-(2-methoxyphenyl)ethyl]amino}butyl)amide Bicyclo[2.2.2]octane-1-carboxylic acid (0.53 g, 3.4 mmol), and thionyl chloride (1 ml, 13 mmol) dissolved in 10 ml toluene, were heated at 80° C. for 3 h. The solvent was partly removed and the residue added dropwise to a solution of 4-{isopropyl-[2-(2-methoxyphenyl)-ethyl]-aminobutylamine (1.2 g, 4.5 mmol) and triethylamine (3 ml, 20 mmol) in 10 ml methylene chloride at 0° C. and stirred for 1 h at room temperature. The mixture was charged on a silica gel column and eluated with hexane/ethyl acetate/triethylamine (16:4:1) to yield 1.1 g (86%) of an oil.

$^1$H NMR (CDCl$_3$) δ 7.15 (dd, 2 H), 6.84 (dd, 2 H), 5.55 (bs, 1 H), 3.81 (s, 3 H), 3.18 (1m, 2 H), 2.98 (m, 1 H), 2.71 (m, 2 H), 2.57 (m, 2 H), 2.45 (t, 2 H), 1.67 (m, 6 H), 1.60 (m, 7 H), 1.45 (m, 4 H), 0.99 (d, 6 H).

In an analogous way the following compound (example 38) was prepared:

Example 38

Adamantane-1-carboxylic acid (4-{isopropyl-[2-(2-methoxy-phenyl)ethyl]amino}butyl)amide $^1$H NMR (CDCl$_3$) δ 7.20–7.11 (m, 2 H), 6.89–6.83 (m, 2 H), 5.6 (s, 1 H), 3.82 (s, 3 H), 3.24–3.21 (m, 2 H), 2.99 (sept, 1 H), 2.75–2.72 (m, 2 H), 2.60–2.55 (m, 2 H), 2.48–2.43 (m, 2 H), 2.06–2.03 (m, 3 H), 1.85–1.84 (m, 6 H), 1.71–1.69 (m, 6 H), 1.48–1.45 (m, 4 H), 1.00 (d, 6 H).

Example 39 (Method E)

Adamantane-1-carboxylic acid (4-{isopropyl-[2-(2-methoxy-phenyl)ethyl]amino}but-2-enyl)amide A mixture of adamantane-1-carboxylic acid (4-{isopropyl-[2-(2-methoxyphenyl)ethyl]amino}but-2-ynyl)amide, (90 mg, 0.21 mmol), nickel chloride hexahydrate (60 mg, 0.25 mmol), ethylenediamine (0.15 ml, 0.25 mmol) and sodium borohydride (0.25 ml 1N solution in EtOH, 0.25 mmol) in 5 ml ethanol was stirred at ambient temperature for 10 h. The mixture was filtered, the solvent removed and the residue taken up in methylene chloride and washed with water. Evaporation of the solvent gave 71 mg of an oil.

$^1$H NMR (CDCl$_3$) δ 7.20–7.11 (m, 2 H), 6.90–6.83 (m, 2 H), 5.75–5.67 (m, 1 H), 5.70 (s, 1 H), 5.85–5.50 (m, 1 H), 3.93 (dd, 1 H), 3.82 (s, 3 H), 3.21 (d, 1 H), 3.03 (sept, 1 H), 2.77–2.72 (m, 2 H), 2.63–2.57 (m, 2 H), 2.06–2.01 (m, 3 H), 1.84–1.83 (m, 6 H), 1.72–1.69 (m, 6 H), 1.03 (d, 6 H).

In an analogous way the following compounds (examples 40–42 were prepared:

Example 40

Cyclohexanecarboxylic acid, N-(4-[2-(2,3-dimethoxyphenyl)etyl]propylamino-cis-but-2-enyl) amide oxalate M.p. 113°–115° C.

Example 41

N-Propyl-N-[2-(2,3-dimethoxphenyl)ethyl]-(4-phthalimido-cis-but-2-enyl)amine $^1$H NMR (CDCl$_3$) 7.86–7.83 (m, 2 H), 7.72–7.69 (m, 2 H), 6.97 (dd, 1 H), 6.80–6.76 (m, 2 H), 5.79–5.70 (m, 2 H), 5.65–5.57 (m 2 H), 4.36 (d, 2 H), 3.85 (s, 3 H), 3.83 (s, 3 H), 3.42 (d, 2 H), 2.81–2.79 (m, 2 H), 2.74–2.69 (m, 2 H), 2.54–2.49 (m, 2 H), 1.57 (sixt., 2 H), 0.90 (t, 3 H).

Example 42

N-Propyl-N-[2-(4-amino-3-trifluoromethylphenyl) ethyl]-(4-phthalimido-cis-but-2-enyl)amine oxalate M.p. 136°–138° C.

Example 43 (Method F)

8-(4-{Isopropyl-[2-(2-hydroxyphenyl)ethyl]amino}-butyl)-8-aza-spiro[4.5]decane-7,9-dione 8-(4-{Isopropyl-[2-(2-methoxyphenyl)ethyl]-amino}butyl)-8-aza-spiro[4.5]decane-7,9-dione (550 mg, 1.2 mmol) dissolved in 10 ml methylene chloride was cooled to –60° C. under nitrogen. Boron tribromide (0.28 ml, 2.9 mmol) in 3 ml methylene chloride was added in 20 min and the mixture stirred at 10° C. overnight, poured into 5 ml cold sodium hydrogen carbonate solution. The aqueous phase was treated with 1M ammonia and extracted with methylene chloride and the solvent evaporated to yield 410 mg of an oil.

$^1$H NMR (CDCl$_3$) δ 8.05 (s, 1 H), 7.09 (t, 1 H), 6.96 (d, 1 H), 6.84 (d, 1 H), 6.72 (t, 1 H), 3.77 (m, 2 H), 3.12 (m, 1 H), 2.77 (m, 2 H), 2.70 (m, 2 H), 2.56 (s, 4 H), 2.52 (m, 2 H), 1.69 (m, 4 H), 1.51 (m, 8 H), 1.00 (d, 6 H).

Example 44 (Method F)

Trifluoro-methanesulfonic acid 2-(2-{[4-(7,9-dioxo-8-aza-spiro[4.5]dec-8-yl)butyl] isopropylamino}ethyl)phenyl ester A solution of the product in example 26 (224 mg, 0.56 mmol) in methylene chloride and triethylamine (74 mg, 0.73 mmol) was cooled to –70° C. under nitrogen. Trifluoromethanesulfonic acid anhydride (190 mg, 0.67 mmol) was added dropwise during 10 min and the mixture warmed to 0° C. and washed with 1M ammonia. The organic phase was dried (MgSO$_4$) and the solvent evaporated to yield 200 mg of an oil.

$^1$H NMR (CDCl$_3$) δ 7.40–7.25 (m, 4 H), 3.75 (t, 2 H), 2.95 (m, 1 H), 2.80 (m, 2 H), 2.64 (m, 2 H), 2.58 (s, 4 H), 2.53 (m, 2 H), 1.70 (m, 4 H), 1.50 (m, 4 H), 1.38 (m, 4 H), 0.94 (d, 6 H).

Example 45 (Method F)

2-(2-{[4-(7,9-Dioxo-8-aza-spiro[4.5]dec-8-yl)butyl]-isopropylamino}ethyl)-N-methylbenzamide To a solution of the product from example 44 (360 mg, 0.68 mmol) in 8 ml dioxan was added palladium acetate (10 mg, 0.04 mmol), 1,3-bis(diphenylphosphinopropane (25 mg, 0.06 mmol) and 4 ml methylamine solution in dioxan in a carbon monoxide atmosphere. The mixture was heated at 80° C. for 16 h. The solvent was removed and the residue dissolved in ethyl acetate and washed with saturated potassium carbonate solution. The organic phase was dried and the solvent removed the residue purified by chromatography to yield 260 mg of an oil.

$^1$H NMR (CDCl$_3$) δ 7.53 (d, 1 H), 7.31 (dd, 1 H), 7.17–7.22 (m, 2 H), 3.61 (t, 2 H), 2.97 (d, 3 H), 2.70–2.90 (m, 5 H), 2.56 (s, 4 H), 2.26 (t, 2 H), 1.67–1.72 (m, 4 H), 1.42–1.50 (m, 4 H), 1.18–1.30 (m, 4 H), 1.89 (d, 6 H).

Example 46 (Method F)

trans-4-Propylcyclohexanecarboxylic acid, 5-{[2-(4-amino-2-chlorophenyl)-ethyl] propylamino}pentylamide dihydrochloride M.p. 125°–130° C.

Example 47 (Method F)

Cyclohexanecarboxylic acid, (4-{[2-(4-amino-3-cyanophenyl)ethyl]propyl-amino}butyl)amide $^1$H NMR (CDCl$_3$) 7.15 (m, 2 H), 6.66 (d, 1 H), 5.75 (s, 1 H), 4.34 (s, 2 H), 3.43 (t, 2 H), 3.19 (m, 2 H), 2.56 (s, 4 H), 2.38 (m, 4 H) 1.95 (m, 5 H), 1.42 (broad, 6 H), 1.22 (broad, 4 H), 0.83 (t, 3 H).

Example 48 (Method H)

Adamantyl-1-carboxylic acid (4-{isopropyl-[2-(2-methoxyphenyl)ethyl]amino}but-2-ynyl)amide A solution of paraformaldehyde (72 mg, 2.4 mmol) and adamantyl-1-carboxylic acid propargylamide (440 mg, 2.0 mmol) in 3 ml dioxan is heated to 50° C. for 1 h. A catalytic amount of copper acetate and N-isopropyl-2-methoxyphenylethylamine (390 mg, 2.0 mmol) are added and the mixture heated at 80° C. for 3 h. After cooling, 10 ml methylene chloride is added and the organic phase washed with water (2×10 ml), the solvent evaporated and the residue purified by chromatograpy (n-hexane/ethyl acetate) to yield 125 mg of an oil $^1$H NMR (CDCl$_3$) δ 7.19–7.13 (m, 2 H), 6.91–6.84 (m, 2 H), 5.7 (s, 1 H), 4.00–4.03 (m, 2 H), 3.83 (s, 3 H), 3.50–3.46 (m, 2 H), 3.04 (sept. 1 H), 2.78–2.71 (m, 4 H), 2.07–2.03 (m, 3 H), 1.84–1.83 (m, 6 H), 1.72–1.69 (m, 6 H), 1.07 (d, 6 H).

In an analogous way the following compound (example 49 was prepared.

Example 49

Cyclohexanecarboxylic acid, N-(4-[2-(2,3-dimethoxyphenyl)-ethyl]-propylaminobut-2-ynyl) amide M.p. 69°–71° C.

Pharmaceutical Preparations

The following examples illustrate suitable pharmaceutical compositions to be used in the method of the invention. For the preparation of tablets the following compositions can be made.

| Composition 1 | |
| --- | --- |
| Compound according to Example 1 | 50 g |
| Lactose | 85 g |
| Potato starch | 40 g |
| Polyvinylpyrrolidone | 5 g |
| Microcrystalline cellulose | 18 g |
| Magnesium stearate | 2 g |
| Composition 2 | |
| Compound according to Example 1 | 100 g |
| Lactose | 90 g |
| Potato starch | 50 g |
| Polyvinylpyrrolidone | 5 g |
| Microcrystalline cellulose | 23 g |
| Magnesium stearate | 2 g |

From the above compositions 1 000 tablets can be made, containing 50 mg and 100 mg of active substance, respectively. If desired, the obtained tablets can be film coated with e.g. hydroxypropyl methyl cellulose in an organic solvent or using water.

Pharmacoloqy

It is generally accepted that drugs that bind to dopamine D2 receptors and are antagonists at these receptors will be clinically effective as antipsychotic agents (for example in schizophrenia). It is also believed that a serotoninergic (5HT1A) receptor affinity as an agonist can be a useful property by reducing the incidence of extrapyramidal side effects and by increasing the efficacy of the substance in psychoses. These substances by having a certain ratio of D2 and 5HT1A binding will retain an antipsychotic effect at the same time as having a reduced incidence of side effects and improved efficacy.

The compounds of the invention exhibit an affinity for D$_3$ receptors. D$_3$ receptors are concentrated in limbic parts of the brain, which means that drugs that have affinity for these receptors may have lower side effect. Some of the compounds also exhibit affinity for 5-HT$_{1A}$ and D$_2$ receptors. These effects make it possible to use the compounds defined above in the treatment of mental disturbances e.g. psychosis, schizophrenia and depression.

The pharmacological methods are described below.

D2 Receptor Binding Assay

Cells and membrane preparation. Mouse fibroblast LTK$^-$ cells expressing human D$_{2(long)}$ receptors were kindly supplied by Dr. O. Civelli (Oregon Health Sciences University) and are grown in Dulbecco's Modified Eagle's Medium (DMEM) supplemented with 10 mM HEPES, 10% fetal calf serum (FCS) in 225 cm$^2$ flasks with ventilated caps (Costar) in 5% CO$_2$ in air at 37° C. The cells are detached with 0.05% trypsin and 0.02% EDTA in PBS (phosphate-buffered saline), centrifuged for 10 min at 300 g, washed in DMEM two additional times and homogenized with a Dounce homogenizer in 10 mM Tris-HCl and 5 mM MgSO$_4$, pH 7.4. The homogenate is washed twice in binding buffer (50 mM Tris-HCl, pH 7.4 with 1 mM EDTA, 5 mM KCl, 1.5 mM CaCl$_2$, 4 mM MgCl$_2$, 120 mM NaCl) by centrifugation for 10 min at 43500 g and stored in aliquots at –70° C.

Receptor binding assay. The frozen cell membranes are thawed, homogenized with a Branson 450 sonifier and suspended in binding buffer to a final receptor concentration of 100 pM. Various concentrations of the test compound, the radioligand (1 nM $^3$H-Raclopride) and the cell homogenate are incubated for 60 min at room temperature. Nonspecific binding is determined by the addition of 1 µM (+)-Butaclamol. The incubation is terminated by rapid filtration through glass fiber filter (Whatman GF/B, pretreated with 0.05% polyethyleneimine) and washed with cold 50 mM Tris-HCl (pH 7.4) using Brandel cell harvest equipment. The radioactivity of the filters is measured in a Liquid Scintillation Analyzer (Packard 2200CA or 2500TR) at an efficiency of about 50% after addition of scintillation cocktail (Packard Ultima Gold, 3 ml). Data is analysed by non-linear regression using the LIGAND program, and presented as K$_i$ values.

5-HT$_{1A}$ Receptor binding Assay

Tissue preparation. The rats are decapitated and the hippocampi are dissected out on ice. The hippocampi are homogenized using an Ultra Turrax in 50 mM Tris-HCl buffer containing 10 mM EDTA, pH 7.4. The homogenate is centrifuged (using Sorvall RC-5B) for ten minutes at 19,500 rpm (43,500× g) and 4° C. The pellet is resuspended in 50 mM Tris-HCl buffer, pH 7.4 and recentrifuged. The final pellet is suspended in 0.32M sucrose and frozen at –20° C. until use. On the day of the assay the frozen homogenate is thawed and suspended in binding buffer (50 mM Tris-HCl buffer, pH 7.4 containing 2 mM CaCl$_2$, 1 mM MgCl$_2$) corresponding to 2.5 mg original wet weight per test tube. The homogenate is preincubated for ten minutes at 37° C. to remove endogenous serotonin whereafter pargylin is added to give a final concentration of 10 µM.

Receptor binding assay. Various concentrations of the test compound (diluted in 0.1% ascorbic acid), the radioligand (1 nM $^3$H-8-OH-DPAT diluted in binding buffer) and the homogenate are incubated at 37° C. for 45 minutes in a final volume of 0.5 ml. The nonspecific binding is obtained as that bound in presence of 100 µM unlabelled serotonin. The incubation is stopped by rapid filtration through glass fiber filters (Whatman GF/B) and subsequent washing with cold 50 mM Tris-HCl buffer pH 7.4, using a cell harvester (Brandel). The radioactivity of the filters is measured in a liquid scintillation spectrometer (Beckman LS5000TD or Packard 2500TR). Data is analysed by non-linear regression using the LIGAND program, and presented as Ki values.

D3 Receptor Binding Assay

Cells and membrane preparation. Chinese hamster ovary (CHO) cells expressing human D$_3$ receptors purchased from Insern Institute, Paris, France are grown in Dulbecco's Modified Eagle's Medium (DMEM) supplemented with 10 mM HEPES, 10% dialysed fetal calf serum (FCS) and PeSt (70 µg/ml benzylpencillin K and 10 µg/ml streptomycin sulphate) in 225 cm$_2$ flasks with ventilated caps (Costar) in 5% $CO_2$ in air at 37° C. The cells are detached with 0.05% trypsin and 0.02% EDTA in PBS (phosphatebuffered saline), centrifuged for 10 min at 300 g, washed in DMEM two additional times and homogenized with a Dounce homogenizer in 10 mM Tris-HCl and 5 mM $MgSO_4$, pH 7.4. The homogenate is washed twice in binding buffer (50 mM Tris-HCl, pH 7.4 with 1 mM EDTA, 5 mM KCl, 1.5 mM $CaCl_2$, 4 mM $MgCl_2$, 120 mM NaCl) by centrifugation for 10 min at 43500 g and stored in aliquots at −70° C.

Receptor binding assay. The frozen cell membranes are thawed, homogenized with a Branson 450 sonifier and suspended in binding buffer to a final receptor concentration of 100 pM. Various concentrations of the test compound, the radioligand (1 nM $^3$H-Raclopride) and the cellhomogenate are incubated for 60 min at room temperature. Nonspecific binding is determined by the addition of 1 µM (+)-Butaclamol. The incubation is terminated by rapid filtration through glass fiber filter (Whatman GF/B, pretreated with 0.05% polyethyleneimine) and washed with cold 50 mM Tris-HCl (pH 7.4) using Brandel cell harvest equipment. The radioactivity of the filters is measured in a Liquid Scintillation Analyzer (Packard 2200CA or 2500TR) at an efficiency of about 50% after addition of scintillation cocktail (Packard Ultima Gold, 3 ml). Data is analysed by non-linear regression using the LIGAND program, and presented as $K_i$ values.

We claim:
1. A compound of formula I

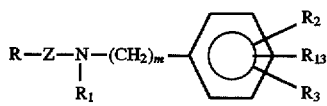

or a pharmaceutically acceptable salt thereof, wherein

Z is a saturated or unsaturated 3-to 6-carbon chain, m is 2 or 3, $R_1$ is a hydrogen atom, or a straight or branched $C_{1-4}$ alkyl group, $R_2$, $R_3$ and $R_{13}$ are situated in the ortho, meta, or para position of the phenyl ring and are the same or different and are selected from the following groups: H, OH, $OR_{14}$, halogen, $CO_2R_9$, CN, $CF_3$, $NO_2$, $NH_2$, $COCH_3$, $OSO_2CF_3$, $OSO_2CH_3$, $CONR_{10}R_{11}$ and $OCOR_{12}$, wherein $R_9$, $R_{12}$ and $R_{14}$ are the same or different and are each a straight or branched $C_{1-4}$ alkyl group, and $R_{10}$ and $R_{11}$ are the same or different and represent hydrogen or a straight or branched $C_{1-6}$ alkyl group, R is 1)

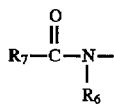

wherein $R_6$ is a hydrogen atom or a straight or branched $C_{1-6}$ alkyl group, and $R_7$ is a substituted or unsubstituted cycloalkyl group, or $R_6$ and $R_7$ are together —$(CH_2)n_2$—, wherein $n_2$ is 3 to 6; or

2)

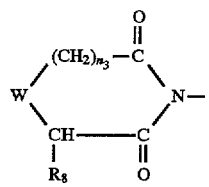

wherein W is an optionally substituted saturated carbocyclic ring(s) or an optionally substituted methylene group, $R_8$ is a straight or branched $C_{1-5}$ alkyl group or a phenyl group, and $n_3$ is 0 to 2; or

3)

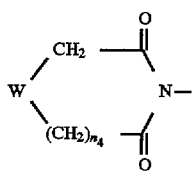

wherein W is an optionally substituted saturated carbocyclic ring(s), or an optionally substituted methylene group and $n_4$ is 1 or 2, in racemic or optically active form, provided that when $R_2$, and $R_3$ together represent 3,4-dimethoxy; m is 2; $R_1$ is H and Z is $CH_2CH_2$, then R is not 1-pyrrolidin-2-one or 1-piperidine-2,6-dione.

2. A compound according to claim 1, wherein R is

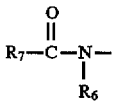

$R_2$ is hydrogen, methoxy, ethoxy, halogen, CN, $CONR_{10}R_{11}$, $CF_3$, nitro or amino, $R_3$ is methoxy, ethoxy, halogen, CN, $CONR_{10}R_{11}$, $CF_3$, nitro or amino, $R_{13}$ is hydrogen, methoxy, ethoxy, halogen, CN, $CONR_{10}R_{11}$, $CF_3$, nitro or amino, and Z is, when saturated, a 3-to 6-carbon chain and, when unsaturated, a 4-to 6-carbon chain.

3. A compound according to claim 1 wherein R is

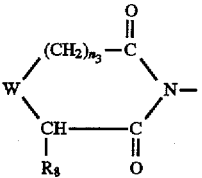

$R_2$ is hydrogen, methoxy, ethoxy, halogen, CN, $CONR_{10}R_{11}$, $CF_3$, nitro or amino, $R_3$ is methoxy, ethoxy, halogen, CN, $CONR_{10}R_{11}$, $CF_3$, nitro or amino, $R_{13}$ is hydrogen, methoxy, ethoxy, halogen, CN, $CONR_{10}R_{11}$, $CF_3$, nitro or amino, and Z is, when saturated, a 3-to 6-carbon chain and, when unsaturated, a 4-to 6-carbon chain.

4. A compound according to claim 1, wherein
R is

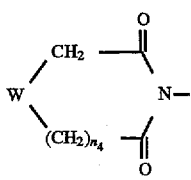

$R_2$ is hydrogen, methoxy, ethoxy, halogen, CN, $CONR_{10}R_{11}$, $CF_3$, nitro or amino, $R_3$ is methoxy, ethoxy, halogen, CN, $CONR_{10}R_{11}$, $CF_3$, nitro or amino, $R_{13}$ is hydrogen, methoxy, ethoxy, halogen, CN, $CONR_{10}R_{11}$, $CF_3$, nitro or amino, and Z is, when saturated, a 3-to 6-carbon chain and, when unsaturated, a 4-to 6-carbon chain.

5. A compound selected from 8-(4-{[2-(4-Amino-3-trifluoromethylphenyl)ethyl] methylamino}butyl)-8-aza-spiro[4.5]decane-7,9-dione oxalate;

Cyclohexanecarboxylic acid (4-{[2-(3,4-dimethoxyphenyl)ethyl]propylamino}butyl)amide;

Cyclohexanecarboxylic acid (4-{[2-(5-bromo-2-methoxyphenyl)ethyl]propylamino}butyl)amide oxalate;

Bicyclo[2.2.2]octane-1-carboxylic acid (6-{[2-(4-amino-3-trifluoromethylphenyl)ethyl]methylamino}-hexyl) amide hydrochloride;

Bicyclo[2.2.2]octane-1-carboxylic acid (4-{isopropyl-[2-(2-methoxyphenyl)ethyl]amino}butyl)amide;

Adamantane-1-carboxylic acid (4-{[2-(3-methoxyphenyl)ethyl]propylamino}butyl)amide oxalate;

Cyclohexanecarboxylic acid (4-{[2-(2-chloro-4-methoxyphenyl)ethyl]propylamino}butyl)amide oxalate;

Adamantane-1-carboxylic acid (4-{[2-(2,4-dimethoxyphenyl)ethyl]propylamino}butyl)amide oxalate; and Cyclohexanecarboxylic acid, (4-{[2-(4-amino-3-cyanophenyl)ethyl]propylamino}butyl)amide.

6. A process for the preparation of a compound of formula I as defined in any one of claims 1, 2, 3, 4 and 5 which comprises A. reaction of a compound of formula II

wherein R and Z are as defined in claim 1 and X is a leaving group or a group

wherein Y is hydrogen, hydoxy, halogen or alkoxy, with a compound of formula III

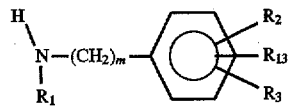

wherein $R_1$, $R_2$, $R_3$, $R_{13}$ and m are as defined in claim 1, or

B. reaction of a compound of formula IV

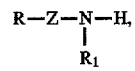

wherein R, Z and $R_1$ are as defined in claim 1, with a compound of formula V

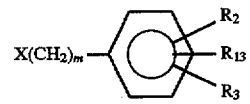

wherein X is as defined above and m, $R_2$, $R_3$ and $R_{13}$ are as defined in claim 1, or C. reaction of a compound of formula VI

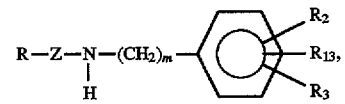

wherein R, Z, m, $R_2$, $R_3$ and $R_{13}$ are as defined in claim 1, with a compound of formula VII

wherein $R_1$ is as defined in claim 1 and X is as defined above, or

D. reaction of a compound of formula VIII

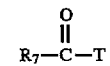

wherein $R_7$ is as defined in claim 1 and T represents an acid derivative, or a compound of the general formula IX

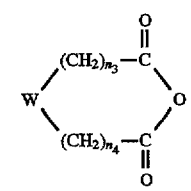

wherein W, $n_3$ and $n_4$ are as defined in claim 1, with a compound of the general formula X

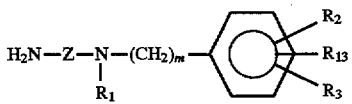

wherein Z, $R_1$, $R_2$, $R_3$, $R_{13}$, and m are as defined in claim 1, or

E. conversion of a compound of formula XI

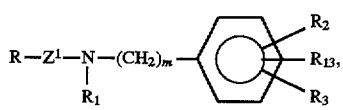

wherein R, $R_1$, $R_2$, $R_3$, $R_{13}$, and m are as defined in claim 1 and $Z^1$ represents an unsaturated 3-to 6-carbon chain, to a compound of formula I

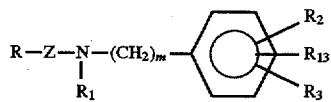

wherein R, $R_1$, $R_2$, $R_3$, $R_{13}$, Z and m are as defined in claim 1, by use of a reducing agent, or F. conversion of a compound of formula XII

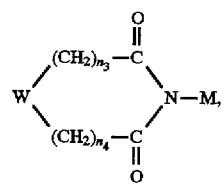

wherein R, $R_1$, Z and m are as defined in claim 1 and $R^1_2$, $R^1_3$ and $R^1_{13}$ represent substituents that can be modified by reduction, hydrogenation, hydrolysis, demethylation, nitration, esterification, halogenation, acetylation, carbonylation (C=O), dehydration or other such reactions to a compound of formula I

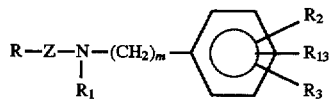

wherein R, $R_1$, $R_2$, $R_3$, $R_{13}$, Z and m are as defined in claim 1, or

G. reaction of a compound of formula XIII

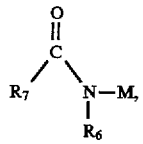

wherein $R_6$ and $R_7$ are as defined in claim 1 and M represents and alkali metal, or reaction of a compound of formula XIV

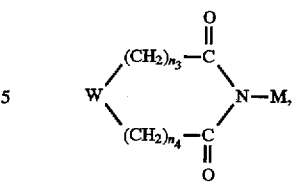

wherein M is as defined above and W, $n_3$ and $n_4$ are as defined in claim 1, with a compound of formula XV

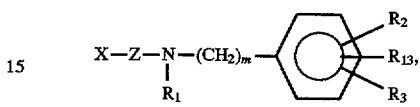

wherein X is as defined above and Z, $R_1$, $R_2$, $R_3$, $R_{13}$ and m are as defined in claim 1, in the presence of a base, or H. reaction of a compound of formula XVI

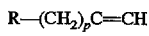

$$R—(CH_2)_pC≡CH$$

wherein R is as defined in claim 1 and p is 1 to 3, with paraformaldehyde and a compound of formula III

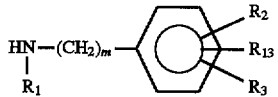

wherein $R_1$, $R_2$, $R_3$, $R_{13}$, and m are as defined in claim 1, whereafter, if so desired the compound obtained by any of the processes A–H is converted to a pharmaceutically acceptable salt thereof or to an optically active form.

7. A pharmaceutical preparation comprising an effective amount of a compound according to any one of claims 1, 2, 3, 4 and 5 as active ingredient in association with a pharmaceutically acceptable carrier.

8. A pharmaceutical preparation according to claim 7 in dosage unit form.

9. A method for the treatment of psychiatric disorders in mammals which comprises administering to a mammal in need of such treatment an effective amount of a compound according to any one of claims 1, 2, 3, 4 and 5.

10. A method of treating abnormalities which are associated with a malfunction of $D_3$ receptor expression in a subject, which comprises administering to the subject an amount of the pharmaceutical composition of claim 7 that will affect the subject's $D_3$ receptors.

* * * * *

UNITED STATES PATENT AND TRADEMARK OFFICE
CERTIFICATE OF CORRECTION

PATENT NO. : 5,693,630
DATED : December 2, 1997
INVENTOR(S) : Bengtsson et al.

It is certified that error appears in the above-indentified patent and that said Letters Patent is hereby corrected as shown below:

col. 20, line 29(claim 1), change " and $R_3$" to --$R_3$ and $R_{13}$--;

col. 21, line 66, change "hydoxy" to --hydroxy--;

col. 23, lines 20-28, change " 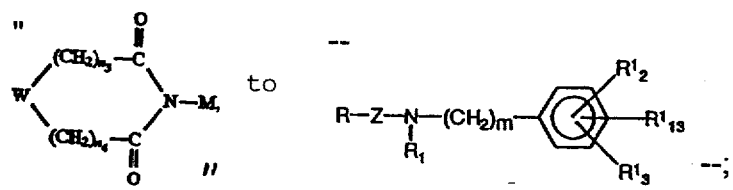 --;

col. 23, line 52, change "and" to --an--, and col. 24, line 23, change "$R-(CH_2)_p C=CH$" to --$R-(CH_2)_p C\equiv CH$--

Signed and Sealed this

Sixteenth Day of June, 1998

Attest:

BRUCE LEHMAN

Attesting Officer    Commissioner of Patents and Trademarks